United States Patent
Gomez (10) Patent No.: US 7,080,641 B2
(45) Date of Patent: Jul. 25, 2006

(54) METHOD AND APPARATUS FOR HEATING STERILE SOLUTIONS DURING MEDICAL PROCEDURES

(76) Inventor: Ricardo Alexander Gomez, 571 Main St., Amherst, MA (US) 01002

( * ) Notice: Subject to any disclaimer, the term of this patent is extended or adjusted under 35 U.S.C. 154(b) by 0 days.

(21) Appl. No.: 10/826,871

(22) Filed: Apr. 16, 2004

(65) Prior Publication Data

US 2005/0230376 A1   Oct. 20, 2005

(51) Int. Cl.
   *F24J 1/00*   (2006.01)
(52) U.S. Cl. .......................... 126/263.09; 126/263.01; 126/263.07
(58) Field of Classification Search .................... None
   See application file for complete search history.

(56) References Cited

U.S. PATENT DOCUMENTS

| | | | |
|---|---|---|---|
| 3,998,208 A | 12/1976 | Abboud | |
| 5,263,116 A | 11/1993 | Hammond | |
| 6,029,613 A | 2/2000 | Ohshima et al. | |
| 6,325,297 B1 | 12/2001 | Calvin et al. | |
| 6,821,539 B1 * | 11/2004 | Lassota | 426/231 |
| 6,870,135 B1 * | 3/2005 | Hamm et al. | 219/386 |
| 2004/0065314 A1 * | 4/2004 | Layer et al. | 126/263.03 |
| 2005/0081841 A1 * | 4/2005 | Schreft et al. | 126/263.09 |

* cited by examiner

*Primary Examiner*—Thor S. Campbell
(74) *Attorney, Agent, or Firm*—McCormick, Paulding & Huber LLP (57) ABSTRACT

An apparatus which is self-contained, disposable, and heated utilized for maintaining and heating sterile solutions during medical procedures. The heating mechanism is chemical, electrical or a combination of both. Further the apparatus serves as a self sealing container for the application of solution. Sterile solutions such as special surgical adhesives thrombolytic or temperature specific drugs can be repeatedly heated and used during medical procedures. The apparatus also serves as method to maintain solutions sterile and heated for long periods of time during medical procedures. Another purpose of the invention is to have the distill end of the scope uniformly and completely coated by submerging it into the solution within the apparatus. Heat is transferred from the solution to the instrument in one example to act as an additional measure to prevent fogging of the lens. This apparatus is ideal for operations where the instrument is used intermittently and repeatedly.

16 Claims, 4 Drawing Sheets

METHOD AND APPARATUS FOR HEATING STERILE SOLUTIONS DURING MEDICAL PROCEDURES

FIELD OF INVENTION

This invention generally relates to the device and method for heating sterile liquid solutions prior to and during medical procedures. More specifically it relates to a single patient use sterile device that contains a reservoir within it. This reservoir can be filled with any sterile solution and upon activation the apparatus as well as the reservoir is quickly heated above body temperature. The apparatus then maintains the solution heated and sterile during any medical procedure. The method relates to the opening of the said device prior to any medical procedure injecting the desired solution inside device, activating the device, and then placing the device within easy reach of doctor. Only immediately prior to the use or application, the sterile warm solution is removed from inside device using a syringe.

BACKGROUND

It is common for different types of liquids and solutions to be used during medical procedures. Liquids range from simple medications to complex chemicals used for intravenous infusion. In surgical procedures different liquid glues and special chemicals are very often needed during the procedures. Newer and more advanced compounds are being introduced regularly into medicine and into revolutionary new surgical interventions. It is a fact that chemical reactions occur much more efficiently and faster as the temperature of the chemicals increase. It is also a fact that the inside of a human body has a temperature of almost 100 degrees Fahrenheit. It is of no surprise that in medicine there are some liquid solutions that also work more efficiently and interact better with the body when they are administered warm. Often times hospital facilities have heated cabinets to heat solutions and water bottles. The problem is that Operating rooms as well as most of the areas designated for performing medical procedures are kept extremely cold. The cold temperature helps prevent infection and microorganism growth. It is not uncommon for the temperature in these rooms to be maintained at 60 degrees. Another problem is that, most procedures require the solutions to be sterile. This creates a problem. First, even if the solutions were kept very warm, a soon as they are introduced into the large cold room would cool down quickly. Second, since the solutions are sterile the must be removed from their containers and maintained separately for when it is needed in the procedure. Having a solution warm and ready at the exact time the doctor needs it during a medical procedure is almost impossible. Solving this problem is useful for the future. For example, there is some evidence that powerful emergency medications that breakdown crucial clots work more effectively if they are administered warm, since it is not easy to have the solution heated immediately prior to its use, this evidence has not been followed up and largely ignored. Also, it is possible that in the future new sterile glues for orthopedic procedures or other compounds for surgery might need to be heated immediately prior to their sterile use.

Prior art has for a long time described mechanisms and devices for heating liquids. Unfortunately, none of these prior devices can be used during most medical procedures and they most definitely cannot be used to heat solutions intended for use in these procedures. The reason is related to sterility. In medicine, all fluids that come in contact with the interior of the human body must be 100% free of bacteria and must be considered sterile. In order for sterile solutions to be heated, they must be heated in a sterile environment. The majority of apparatuses designed to heat liquids function using electricity. Due to the delicate electrical parts, these apparatuses can not be sterilized. It is not only the part that comes in contact with the liquid that must be sterile; the entire apparatus must be sterile in order to be within the sterile operative field. Even if the current apparatuses designed to heat solutions could be sterilized would still be inadequate for several reasons. They are large and bulky making them unlikely to be used during medical procedures where instrument and supply space is very limited.

Second, their complicated electrical design makes them expensive and prohibitive for widespread use during medical procedures. Additionally, even if the machines could be purchased by the hospital the cost related to sterilizing them every case would in it self be prohibitive. Not to mention that equipment that is re sterilized in the hospital carry a greater risk for infection compared to single use disposable sterile supplies. In order to adequately solve the problem what is needed is a sterile, single patient use, disposable device. To allow for widespread use, the device must be inexpensive as well as small so that it does not take up a great deal of space. The device must be able to heat solutions quickly and also maintain the solutions heated and sterile for at least the entire length of the procedure. It is important for the device to also allow the doctor or nurse too quickly and easily insert and remove solutions from inside the apparatus. Finally, the device must be safe for use during medical procedures.

SUMMARY OF THE INVENTION

It is the object of the present invention to provide a method and an apparatus for heating sterile liquid solutions prior to using the solution during a medical procedure.

It is also the object of the present invention to provide a method and an apparatus for maintaining solutions heated and sterile during a medical procedure.

The present invention entails a small, single patient use, disposable device containing an interior reservoir as well as a heating mechanism surrounding the reservoir When the heating mechanism is activated the reservoir is heated and maintained warm for a sustained period of time.

The present invention entails a method by which the device is sterile and it is opened prior to beginning a medical procedure. This invention consists of a large reservoir inside the center of the apparatus. The opening of the reservoir is open to the exterior of the apparatus. After the apparatus is opened on to the supply table, the nurse or doctor can place any solution they desire, with aseptic technique, inside of the reservoir within the device. Inside the device, surrounding the reservoir is a heat generating mechanism. After the liquid is inside the apparatus. The doctor or nurse activates the heating mechanism from the outside. The reservoir is quickly heated, thereby also heating the solution inside. The heating mechanism stays activated for at least the length of the procedure and continues to heat the reservoir until the mechanism runs out of energy or the device is thrown out. Heated solutions can be removed and used from the reservoir during the procedure. Also, new cold solutions can be reinserted inside reservoir and they will be heated again as frequently as needed during the procedure. The apparatus also contains a one way valve mechanism to prevent fluid from spilling out of the reservoir if the apparatus is turned upside down. The device may also be constructed already containing the liquid or chemicals already within the reservoir. When needed, the device is activated and the liquid is quickly heated and maintained hot, the liquid is then only removed from reservoir when the doctor requests it.

BRIEF DESCRIPTION OF THE SEVERAL VIEWS OF THE DRAWING

These objects and features of the invention will be more clearly understood from the following detailed description along with the accompanying drawing figures, wherein:

FIG. 5–6. Views showing the activation of the heating mechanism.

DETAILED DESCRIPTION OF THE INVENTION

Figure 1:
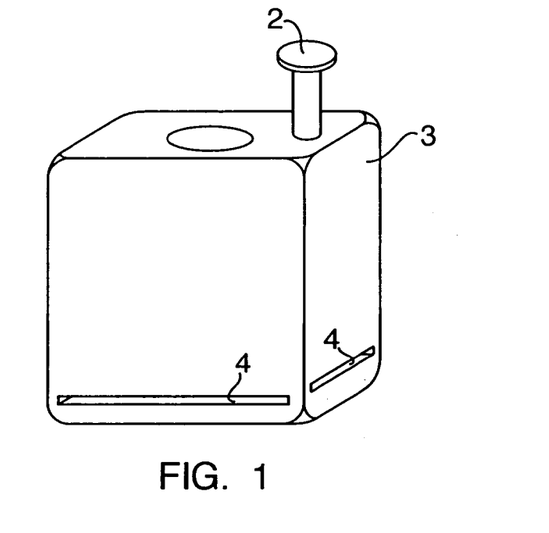
FIG. 1. An external 3-D view of the apparatus.
Figure 2:
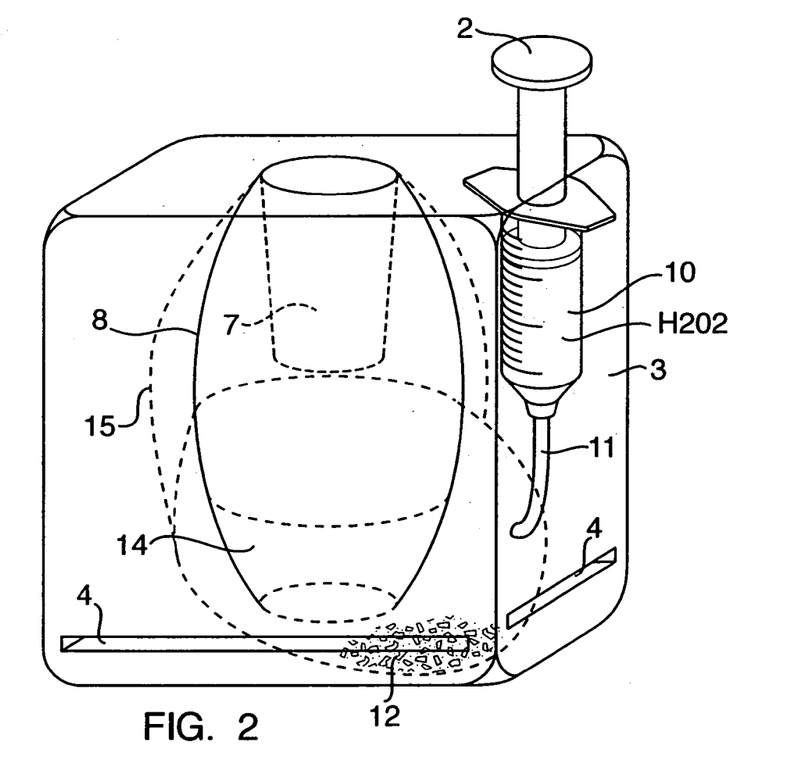
FIG. 2. A Transparent 3-D view of the apparatus with internal components

In one particular embodiment the apparatus described in this invention comprises of an outer shell (3) made of an insolating foam material or any solid which can be shock absorbing insulating material. This shell can be designed to protect the lens of the scope or any other type of instrument from damage prior, during, and after the procedure. The material has to also be inexpensive since the apparatus is disposable and for single patient use. The outer shell cover is preferably constructed of any high density Polyurethane, Etha, Viscoelastic, Latex foams, or the like. It can also be made from rubber foam. A Semi-flexible thermoplastic can also be used. The outer shell can also be made from Insulating cardboard or a thick insulating fabric. The outer shell can alternatively be constructed out of a plastic frame covered by a silicone rubber or insulating plastic. It is important that the material have good shock absorbing and insulating properties The outer shell is preferably cubed shaped as in FIG. 1 but can alternatively be made in any shape; square or spherical.

Figure 3A:
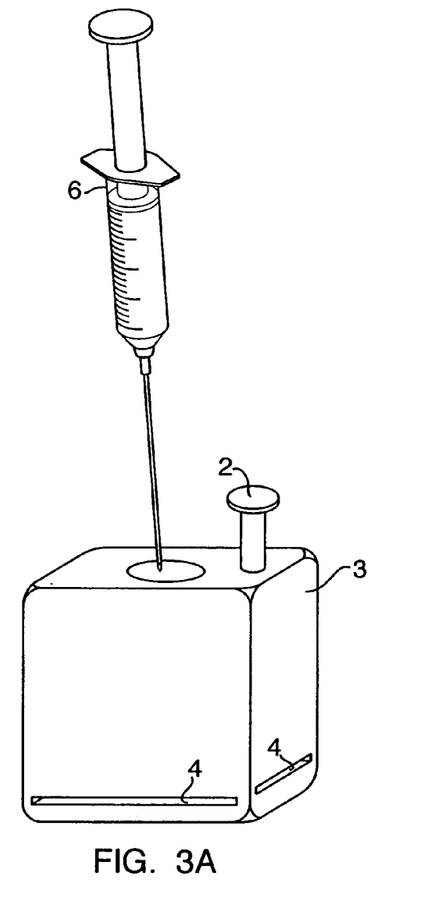
FIGS. 3A and 3B, Depictions of how liquid solutions can be inserted and removed from inside the apparatus using a sterile syringe and a needle.
Figure 3B:
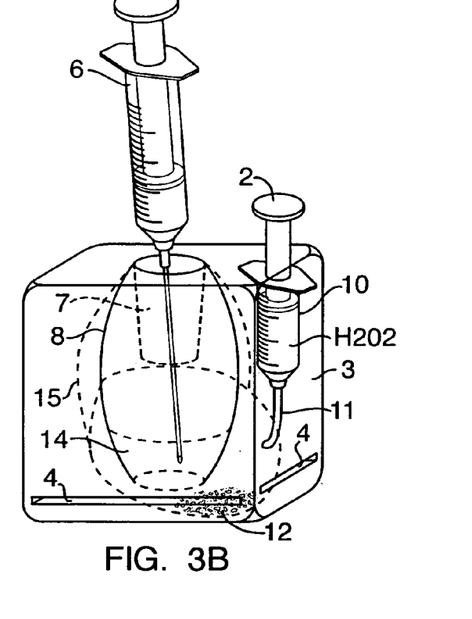

The apparatus can also have a tubular shape. The apparatus can have rounded corners or square corner. The entire apparatus exteriorly is preferably 4 inches long, 3.5 inches wide, and 4 inches high but can be as small as 2 inches wide and 2 inches long and 2 inches high. Alternatively the apparatus can be as large as 6 inches wide, 6 inches long and 8 inches high. Clearly, the apparatus can be sized to conform the shape of any instrument used. Any type of solution (14) may be prepackaged with the apparatus. Alternatively, the apparatus may be filled with solution (14) prior to use and refilled during use. One method to fill the apparatus as shown in FIGS. 3A and 3B is with the use of a syringe (6). Nevertheless, any form of refilling the apparatus may be utilized which is commonly known to persons skilled in the art. This apparatus is not limited to any particular type of solution like anti-fog solution but may be utilized with any solutions necessary for a medical case.

An alternate embodiment, may include on the bottom of the outer shell contains solid flap, which can have the same perimeter as the base of the outer shell. This flap is attached only at the front bottom part of the apparatus creating a hinge. The flap is also attached in the middle by two elastic bands. The flap can be constructed of a high-density foam material, cardboard or plastic. The external face constructed of a high-density foam material, cardboard or plastic. The external face of the bottom flap has an adhesive material that has a protective cover until it is needed. When the surgery begins and the surgeon brings the apparatus up to the operative field he can secure the apparatus anywhere on top of the drapes by removing the protective cover from adhesive bottom and sticking the apparatus anywhere on the operative filed. The function of the flap is so that the scope can be inserted vertically but when it is not in use, is the flap mechanism allows the apparatus to rotate horizontally while the scope remains inside the apparatus. Although the apparatus rotates along the hinge, the flap maintains it securely attached to the drapes by the adhesive flap. Alternatively, the apparatus may be constructed without the flap and the adhesive can be placed directly on the bottom of the apparatus. Also the apparatus can be secured on any surface through such devices as but not limited to: adhesives, screws, magnetism, mounts, clips, or hook and loop fasteners such as those sold under the name VELCRO.

The exterior of the apparatus may contain a soft, non-scratch, absorbent sponge in the uppermost part. The sponge can be square in shape or in the shape of a rectangle. Alternatively the sponge can be in the shape of an eclipse or a circle. The sponge can be ¼ to ¹⁄₁₆ of an inch thick. This sponge is used to wipe the excess defogging solution from the scope after it is removed from the apparatus and can also help with cleaning blood from the scope when it is removed from body cavity.

Internally the apparatus contains a center sheath. This center sheath has a center canal that accommodates the scope. This sheath preferably runs directly down the center or the apparatus from the upper front to the lower back. The sheath can alternatively run directly down the center or lateral to the center. The location of the sheath can be in any configuration as long as uniform thermal conductivity is achieved. The length of the sheath is preferably 3 inches long but can be as long as 8 inches. The sheath has the shape of a tube but can also be constructed of two flat pieces attached together in the upper and lower thirds leaving a tubular canal in the middle. The tubular space inside the sheath can be 5 mm or up to 10 mm, or any length depending on the instrument intended to be used. One embodiment of the sheath is preferably constructed of but not limited to a thin piece of high-density Polyurethane, Etha, Viscoelastic or Latex foams. It can also be made of rubber foam or thin plastic. A water impermeable fabric can also be use. The sheath can alternatively be constructed of silicone or rubber.

The most distal or innermost part of the center sheath (7) penetrates a reservoir (8). This reservoir can be constructed of the same material as the sheath but is preferably made from a metal or any good heat conducting metal such as iron, aluminum, steel, and copper. The reservoir itself can also be made of a magnetic metal material. The reservoir can be in the shape of a box or a cylinder (8). It can be anywhere from ½ an inch to 2 inches long and wide enough to accommodate at least a 5 mm to 10 mm scope and still allow some space around the scope. The reservoir is preferably filled with a defogging solution (14). The defogging solution can be made of a combination of water, glycol, and a water-soluble wetting agent but not limited to such. Alternatively, the defogging solution used can be any commercially available surgical defogging solution such as F.R.E.D™. The reservoir can also be filled with only plain water or saline. Ideally any chemical able to enhance or facilitate the use of an instrument may be used.

Figure 7:
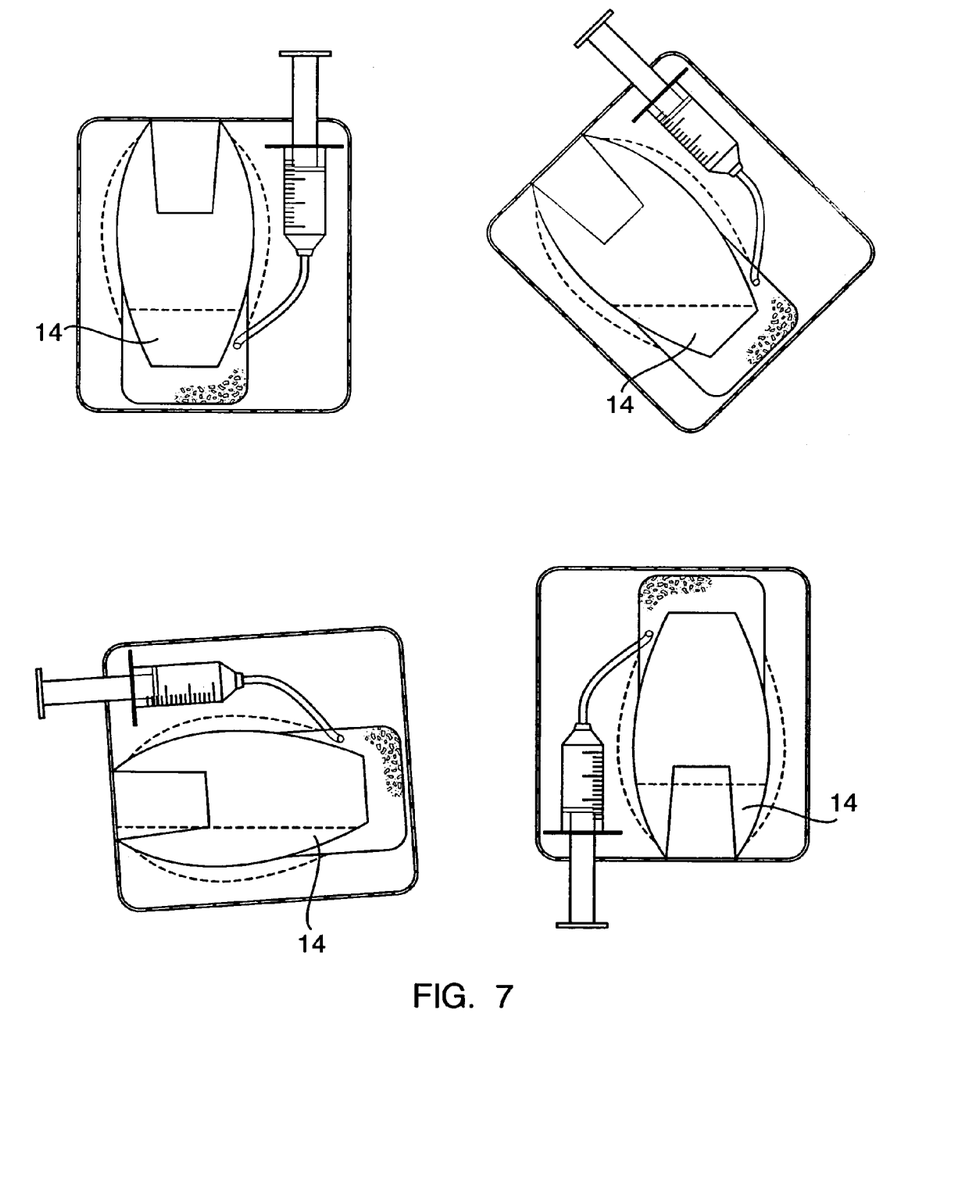
FIG. 7. View showing the apparatus being turned upside down to illustrate how the tubular channel connecting the outside to the inside of the reservoir works as a one way valve to prevent fluid from inside the reservoir to spill out.

Internally, inside the canal between the reservoir filled with defogging solution and the central sheath is a valve mechanism (7). The valve mechanism is preferably constructed by enclosing the reservoir around the distal aspect of the sheath while at least 1 inch overhangs . . . The valve mechanism preferably resembles a tube within a tube. The tube within a tube mechanism that allows for the scope to enter the reservoir and make contact with the solution but prevents any fluid from spilling out of the reservoir when the apparatus is turned upside down with the scope removed. The way it liquid is prevented from falling out functions by creating a pocket around the distil end of the sheath. When the sheath is turned with the reservoir down all the liquid will fall into the reservoir. As the sheath and reservoir are turned upside down, the liquid slides along the side and enters the pocket surrounding the distal sheath. Alternatively, the valve mechanism can also resemble a heart valve or be made with a flap and a hinge that only opens in one direction. The valve can also resemble a valve in a human vein. The valve can be a ball and socket mechanism in which a ball inside the reservoir plugs the hole when the reservoir is turned upside down but still allows for the scope to enter in the other direction. The valve mechanism can be constructed from a plastic material. It can also be made from the same material used for the sheath such as a high-density foam or water impermeable fabric. The valve can also be made of metal, aluminum, or silicone. The valve can be any self sealing mechanism known to person skilled in the art to prevent leakage and splash black of fluid.

The entire center sheath including the distal reservoir segment is surrounded by compound, that is unoxidized but can become easily oxidized and release heat energy when it is oxidized (15). Oxidation reactions are always exothermic, meaning that they always release heat. Metal compounds share the common characteristic that when in their elemental form they are prone to donate electrons and are easily oxidized. The metal preferably used to surround the sheath would be Iron or Fe. The iron is preferably in powder form but can be in pellets or as shavings garnering a large reactive surface area. The Iron used is preferably a commercially available mixture, which uses a combination or Iron, vercumilite, activated charcoal, and water. This commercially available mixture from (mycoal) or (heatmax) can provide up to 6 hours of heat when the iron is oxidized by atmospheric oxygen. Other metals such as Mg, Aluminum, Nickel or Copper can also be used. Unoxidized Non-metals can also be used in gas, powder, or liquid form. The material is preferably in an oxygen permeable membrane wrapped around the sheath. The amount of material surrounding the sheath can as thin as ⅛ of an inch to as thick as to fill the entire upper chamber. The unoxidized material can also be in liquid form surrounding the sheath and reservoir. It can also be in a bag surrounding the sheath and reservoir. The bag can be made of plastic or impermeable rubber foam. Any combination of reactants known to persons skilled in the art can be utilized to create the exothermic reaction.

The one embodiment for heating the defogging solution inside the reservoir as well as the long lasting sustained heating of the apparatus uses three separate exothermic reactions The first reaction uses the energy generated from a fast exothermic decomposition of Hydrogen Peroxide to heat the reservoir very quickly. The second reaction is a slower but consistent decomposition of H2O2. The third reaction uses the oxygen molecules generated in the first and second reaction to slowly oxidize the iron material surrounding the upper part of the reservoir and the central sheath and heat the apparatus for a longer sustained period of time.

Hydrogen peroxide (H2O2) is an unstable molecule, which quickly and spontaneously decomposes to H2O (water) and O2 (oxygen gas). The balanced equation of the reaction is H2O2+H2O2=2H2O+O2. This decomposition reaction is very exothermic. Although H2O2 decomposes spontaneously the rate is much to slow at room temperature. A catalyst is a molecule that facilitates and speeds up the rate of a given reaction. When a catalyst is added to H2O2 the decomposition of H2O2 speeds up greatly causing the H2O2 solution to heat up a large quantities of Oxygen gas are released. By controlling the amount of catalyst one can control the amount of Oxygen gas generated and the amount of heat released to the solution. In the preferred mechanism the catalyst used is Iron oxide. Alternatively the catalyst can be any molecule that speeds up the decomposition of H2O2. Alternatively catalysts such as manganese dioxide, manganese (IV) oxide, silver catalyst, and potassium permanganate can also be used. The natural enzyme, catalaze that is designed to decompose H2O2 in plants and yeast can also be used. The catalyst is preferably in powdered form or in pellets. It can also be in shavings, crystals, and salt or in liquid form. The Shape and type of catalyst determines the precise rate of H2O2 decomposition. The Powdered form of catalyst is much more reactive than the pellet form because of the larger surface area.

The mechanism for activation and function of the preferred heating method. This method accomplishes two things. Upon activation, a fast reaction occurs and the solution in the reservoir is almost immediately heated above body temperature, the heated solution is then maintained above body temperature along with the interior of the apparatus for up to 7 hours.

Figure 4:
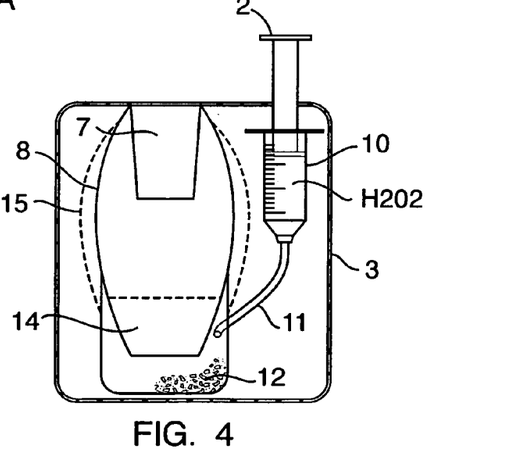
FIG. 4. A view of the internal components of the apparatus including the reservoir and the heating mechanism as well as the activating mechanism.

All the components for an embodiment of the exothermic reaction. The interior of the apparatus comprises two chambers. One upper chamber, which contains the unoxidized material (15) surrounding the sheath and a lower H2O2 containing chamber (10) The H2O2 is contained in a thermo plastic container. The container can alternatively by made from aluminum, copper, iron or any material suitable commonly known to persons skilled in the art. The H2O2 can also be kept in high-density Polyurethane, Etha, Viscoelastic or Latex foam or rubber foam container or any non reactive materials. The H2O2 could also be maintained in a heat resistant plastic or silicone bag. The H2O2 is preferably maintained in a syringe which is connected to the lower part of the apparatus. Alternatively the H2O2 can also be stored in the back or upper part of apparatus. The H2O2 can also be maintained in a container outside the apparatus.

The H2O2 is stored in one embodiment, in a plastic chamber that also contains a cup shaped indentation, vacuole at the top part of the of the container. The indentation creates a space, which surrounds the reservoir (8). Preferably there is a bag or a space surrounding the reservoir. The bag can be made from silicone, plastic or rubber. Inside the space surrounding the reservoir there is a small amount of powdered iron oxide catalysts. This catalyst is found between the reservoir and the internal floor of the cup shaped indentation or inside the bag or chamber around reservoir. The indentation is at least large and deep enough to fit the reservoir and the surrounding unoxidized material. The indented cup exterior is inside the bottom chamber and is surrounded by H2O2 since it penetrates any where from ½ inch to three inches inside the H2O2 container. The external bottom of the cup shaped indentation contains a magnet The indentation in the H2O2 filled container can be any shape as to allow the reservoir bottom and sides to be in direct contact with the H2O2, only separated by the plastic or material that makes up the wall of the H2O2 filled chamber. The cup shaped indentation can alternatively be devoid of a magnet. Alternatively the H2O2 can be completely separate without any indentation, and the reservoir can just sit above the H2O2 receptacle. In this specific mechanism, the H2O2 filled container has a hole in the uppermost part of the chamber. This hole is sealed by a thin film. Sitting directly above the film-covered hole in the upper chamber, is a cylinder or hollow tubular container with one open end directly making contact with the film seal covering the hole. Preferably the hollow cylinder is made from plastic. The seal can also be constructed of aluminum, metal, ceramic, or any other suitable material known to persons skilled in the art. The film sealing the hole in the H2O2 filled container can be constructed of a thin plastic or aluminum paper or a thin water impermeable paper or fabric. Alternatively a one-way valve that is normally closed but can be opened when the plunger cylinder pushes through can also be used to create the seal.

The tubular hollow container sitting directly above the film-covered hole is filled with the iron oxide catalyst (12). The iron oxide catalyst is preferably in shavings or small pellets (12) the amount and shape of the catalyst controls the rate in which the decomposition of H2O2 occurs thereby controlling the generation of heat and oxygen. The Film covered hole on the upper wall of the H2O2 container is at least as wide as to allow the catalyst filled cylinder to slide trough. The uppermost part of the cylinder is closed ended and has a solid extension to the exterior of the apparatus (2). The extension can be a small plastic rod. Alternatively it can be a wooden, metal or aluminum rod. This extension has a flat part in the exterior of the apparatus (2). Alternatively, the cylinder can be made without a plunger extension and the cylinder itself can be long enough to penetrate to the exterior of the apparatus. Any method commonly known to persons skilled in the art can be utilized to initiate the exothermic reaction.

In the upper part of the catalyst filled cylinder is a small tube (11). This tube is open on both ends. One open end is inside the catalyst filled cylinder and the other open end is inside the cup shaped indented space surrounding the reservoir The tube creates an open communication between the inside of the catalyst filled cylinder and the space containing powdered catalyst surrounding the reservoir(8). The tube is preferably constructed out of flexible plastic, or rubber. Silicone, PVC, copper or aluminum tubing can also be used but is not limited to such.

Figure 5:
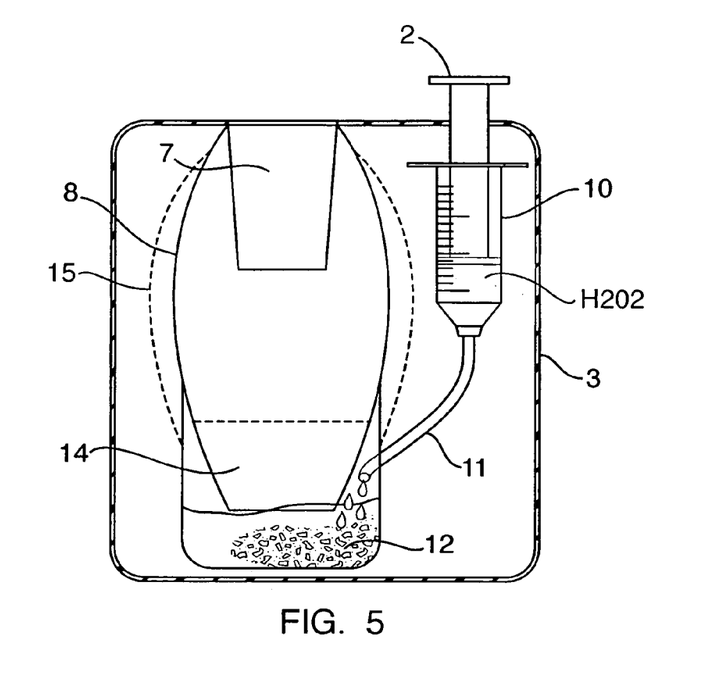
FIG. 5. View of the first step in activation. Plunger is pushed from the exterior. The plunger pushes into the syringe there by pushing the H2O2 out through the tube and into the bag surrounding the reservoir. Inside the bag is a catalyst (Iron oxide). Immediately upon mixing of the H2O2 with the catalyst the H2O2 begins to rapidly decompose. The heat generated from the reaction quickly heats the reservoir and solution inside reservoir.
Figure 6:
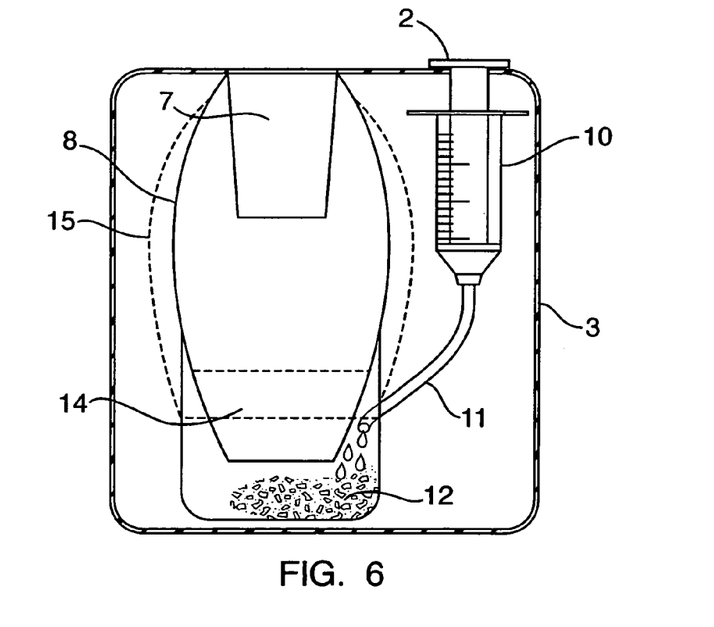
FIG. 6. View of the final step in activation. The plunger is fully inserted and all of the H2O2 is completely introduced to the bag surrounding the reservoir. As the H2O2 decomposes it releases Oxygen gas. The gas escapes through the upper part of the bag and immediately reacts with the Exothermic heat pack surrounding the reservoir. This initiates the heat pack to begin heating. After the oxygen runs out from the first reaction, the heat pack continues to heat by using atmospheric oxygen which comes in through the vents (4) on the outside of the apparatus.

The first step of one embodiment in the activation of the exothermic reaction. Plunger is pushed from the exterior. The plunger pushes into the syringe thereby pushing the H2O2 out through the tube and into the bag surrounding the reservoir. Inside the bag is a catalyst (Iron oxide). Immediately upon mixing of the H2O2 with the catalyst the H2O2 begins to rapidly decompose. The heat generated from the reaction quickly heats the reservoir and solution inside reservoir. The plunger is fully inserted and all of the H2O2 is completely introduced to the bag surrounding the reservoir. As the H2O2 decomposes it releases Oxygen gas. The gas escapes through the upper part of the bag and immediately reacts with the Exothermic heat pack surrounding the reservoir. This initiates the heat pack to begin heating. After the oxygen runs out from the first reaction, the heat pack continues to heat by using atmospheric oxygen which comes in through the vents (4) on the outside of the apparatus. In another mechanism, when activation is desired, downward pressure is applied to the external flat part (2) of the extension (2) of the catalyst-containing cylinder. Once the downward pressure is sufficient enough, the catalyst-containing cylinder will break through the film or seal separating the lower chamber the catalyst-containing cylinder will then enter the lower H2O2 containing chamber. The cylinder is pushed about an inch deep into the H2O2 solution. Once the cylinder breaks the seal gravity will cause the Iron oxide pellets to fall out of the cylinder and enter the H2O2 solution. The H2O2 solution then begins to slowly decompose at a controlled speed that is dependant on the quantity and shape of the catalyst. As soon as the iron oxide catalyst fall out of the cylinder and enter the H2O2 solution the iron oxide pellets are attracted to the magnet located in the external bottom of the cup shaped indentation. This causes all of the catalyst (12) to congregate around the magnet. By having all of the catalyst congregate around the magnet, the H2O2 decomposition will only occur around the external aspect of the cup shaped indentation. The heat generated from the decomposition is therefore much more efficiently transferred to the space around the reservoir allowing for faster heating of the defogging solution in the reservoir. Alternatively the catalyst can also be introduced by having a double close ended, thin walled glass tube filled with the catalyst. When desired, the glass tube is broken and the catalyst is consequently introduced to the H2O2. Another method is to use a liquid catalyst and maintain it in a container or bag above or adjacent to the H2O2. When desired, a seal dividing the liquid catalyst and the H2O2 can be broken and the liquid catalyst is allowed drip into the H2O2. The rate of the decomposition and the amount of O2 generated can then be controlled by the rate and amount of the catalyst drip. Once the catalyst is introduced to the H2O2 chamber, the H2O2 begins to decompose at any predetermined rate.

The H2O2 begins to decompose into H2O and O2 gas the gas rises up to the top of the H2O2 containing chamber. The O2 gas building up in the top part of the H2O2 containing chamber. As more and more O2 is generated the pressure begins to rise. The pressure of the O2 gas pushes on the liquid and the H2O2 surrounding the cylinder begins to be pushed inside the cylinder. As the O2 pressure continues to raise even more the H2O2 that entered the cylinder is pushed in further. The H2O2 enters the small tube (11) and then flows out of the distal end of the tube and into the interior of the indented cup shaped space. Since the H2O2 that enters the space around the reservoir is a small amount and the powdered iron oxide catalyst has a large surface area, the H2O2 decomposes vigorously when it makes contact with the powdered iron catalyst. Large amounts of heat are quickly released and transferred to the reservoir. Since this reaction occurs in direct contact with the reservoir containing defogging solution (8) the solution inside the reservoir is virtually instantaneously heated. At the same time a bolus of Oxygen gas is generated inside the space from the fast decomposition reaction. This Oxygen gas quickly rises into the upper chamber and begins to exothermically oxidize the Iron Material (15) thereby heating the sheath and upper part of the reservoir. The O2 gas continues to be generated in the lower chamber increasing the pressure even more. The Oxygen gas travels into the empty cylinder and then into the tube (11) pushing out all the remaining H2O2 into the space around the reservoir. After the ejection of the H2O2 into the indented space, the level of the H2O2 in the lower chamber becomes lower than the opening of the cylinder, H2O2 cannot enter the cylinder anymore and only the O2 gas generated passes into the cylinder. Once all of the H2O2 has completely entered the indented cup shaped space The O2 gas that is slowly generated in the lower compartment flows through the hollow cylinder and into the tube then out to the indented space where it quickly rises into the upper chamber. As the oxygen begins to fill the middle chamber, the unoxidized iron material begins to get oxidized by the O2 gas. This exothermic reaction is much slower than the decomposition reaction since the O2 is introduced slowly, and thus the heating can be sustained for a long period of time. As the material exothermically oxidizes, heat is generated and transferred to both the sheath and reservoir, maintaining a sustained elevated temperature inside the apparatus. The interior of the apparatus and the solution inside the reservoir are maintained heated by both the heat generated by the H2O2 decomposition occurring in the lower chamber directly below the reservoir and also by the slow exothermic oxidation of the iron material in the upper chamber. The exothermic reaction can be sustained as long as desired by manipulating several factors. The quantity and concentration of the Hydrogen Peroxide, the rate of oxygen generation, which is determined by the speed of the decomposition reaction, and by the amount of, unoxidized iron material in the upper chamber. By generating the oxygen the apparatus can be self-contained and sealed completely from the environment as oppose to depending on atmospheric oxygen as the oxidizing agent. Also, by generating the oxidizing agent, one is able to control the amount and rate at which the oxygen is delivered, thus giving one control over the length of the exothermic reaction, speed of initiation, and the maximum temperature of the exothermic reaction.

The Oxygen molecule is preferably generated by the decomposition of 6% Hydrogen Peroxide but other concentrations below 30% will work. Alternatively, Oxygen can be generated from the decomposition of Potassium chlorate (KclO3). Also the oxygen can be generated from decomposition of oxides such as nitric oxide or Manganese dioxide. Oxygen molecules can also be generated by decomposition of salts such as Potassium nitrate. Oxygen can also be generated by the chemical decomposition of water or the electrolysis of water. The oxygen molecules can also come from atmospheric oxygen found in air.

The oxygen can be generated from the combination of two or more of the above methods. For example, some part of the oxygen can come from the decomposition of one of the mentioned chemicals and another part of the oxygen may come from atmospheric oxygen by way of a vent or opening in the exterior of the apparatus(8).

The heating of the apparatus and reservoir can alternatively be heated by using only atmospheric oxygen. The apparatus may contain small vents in the exterior (4). These vents can be covered by a seal. When the seal is removed the interior is exposed to atmospheric oxygen, therefore oxidizing the material around the sheath and reservoir heating the apparatus and the defogging solution in the reservoir The exothermic reaction can alternatively only contain two reactions. One is preferably a fast initial reaction that is used to quickly heat the reservoir containing defogging solution or saline. The second reaction is a slower sustained reaction that maintains the temperature within the apparatus above body temperature for a longer period of time.

The initial fast heating of the reservoir is preferably attained by the highly exothermic decomposition of H2O2. Alternatively the fast reaction can be generated from other chemicals such as Sodium acetate and water, Calcium chloride and water. Alternatively a battery and a heating filament can be used to heat the reservoir during the initial fast heating part of the dual reaction.

The second, slower, longer lasting reaction is preferably the oxidation of an iron mixture that contains Iron, vercumulite, water and activated charcoal. The sustained longer reaction can also be a combination of two chemicals located around the sheath. The chemicals can be H2O2, Calcium chloride and water or Sodium acetate and water. It can also be two chemicals that when combined form an exothermic reduction oxidation reaction. Alternatively, energy from a battery may also be used to heat the interior of the apparatus and maintain the temperature of the reservoir above body temperature for a sustained period of time.

A multiplicity of exothermic reactions may occur with a multiplicity of different reactants commonly known to persons skilled in the art.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below

What is claimed is:

1. A sterile apparatus for a sustained heating of solution(s) utilized in a medical procedure comprising:
    an impact resistant housing having an outer surface defining an opening, an interior of the housing defining a canal having a first end communicating with the opening and a second end terminating within the housing for receiving a distal lens of an endoscope;
    a solution disposed adjacent to the second end of the canal;
    the interior of the housing further defining a pocket adjacent to the second end of the canal;
    a catalyst disposed in the pocket;
    the interior of the housing further defining a chamber;
    an unoxidized exothermically decomposable material disposed within the chamber; and
    a connector communicating at one end with the chamber and at another end with the pocket for controllably admitting the material into the pocket for activating an exothermic reaction of the material to heat the solution.

2. An apparatus for heating solution(s) to be utilized in a medical procedure as in claim 1, wherein the apparatus is configured to be disposable.

3. An apparatus for heating solution(s) to be utilized in a medical procedure as in claim 1, wherein the apparatus is configured to be sealed prior to utilization of the apparatus.

4. An apparatus for heating solution(s) to be utilized in a medical procedure as in claim 1, further comprising a valve mechanism(s) disposed within the canal to prevent spillage of the solution.

5. An apparatus for heating solution(s) to be utilized in a medical procedure as in claim 1, wherein the solution is prepackaged in the apparatus.

6. An apparatus for heating solution(s) to be utilized in a medical procedure as in claim 1, wherein the solution includes a defogging solution.

7. An apparatus for heating solution(s) to be utilized in a medical procedure as in claim 1, wherein the catalyst includes iron oxide.

8. An apparatus for heating solution(s) to be utilized in a medical procedure as in claim 7, wherein the iron oxide is in the form of at least one of powdered form and pellets.

9. An apparatus for heating solution(s) to be utilized in a medical procedure as in claim 1, wherein the unoxidized exothermically decomposable material includes hydrogen peroxide.

10. An apparatus for heating solution(s) to be utilized in a medical procedure as in claim 1, further comprising a syringe disposed within the chamber, the syringe holding the unoxidized exothermically decomposable material and configured for controllably releasing the material into the pocket via the connector.

11. An apparatus for heating solution(s) to be utilized in a medical procedure as in claim 1, further comprising a securing mechanism on the outer surface of the housing in order to be fastened to a surface.

12. An apparatus for heating solution(s) to be utilized in a medical procedure as in claim 11, wherein the securing mechanism is configured to be removably securable to a surface.

13. An apparatus for heating solution(s) to be utilized in a medical procedure as in claim 11, wherein the securing mechanism is glue.

14. (Currently Amended) An apparatus for heating solution(s) to be utilized in a medical procedure as in claim 11, wherein the securing mechanism is a hook and loop fastener.

15. An apparatus for heating solution(s) to be utilized in a medical procedure as in claim 11, wherein the securing mechanism is a bolt.

16. An apparatus for heating solution(s) to be utilized in a medical procedure as in claim 11, wherein the securing mechanism is a base mechanism permanently securable to a surface.

* * * * *